United States Patent [19]

Amaki et al.

[11] Patent Number: 4,737,146
[45] Date of Patent: Apr. 12, 1988

[54] MULTI-LUMEN EPIDURAL CATHETER

[76] Inventors: Yoshikiyo Amaki, 19-5, Oyamakanaicho, Itabashiku, Tokyo; Osamu Nagano, 603, Dorufumeguro, 17-11, Megurohoncho 3-chome, Meguroku, Tokyo, both of Japan

[21] Appl. No.: 42,615

[22] Filed: Apr. 20, 1987

Related U.S. Application Data

[60] Division of Ser. No. 445,616, Nov. 30, 1982, abandoned, which is a continuation of Ser. No. 218,987, Dec. 22, 1980, abandoned.

[30] Foreign Application Priority Data

Dec. 25, 1979 [JP] Japan ............................ 52-178799

[51] Int. Cl.⁴ ...................... A61M 25/00; A61M 5/00
[52] U.S. Cl. ........................................ 604/51; 604/43; 604/158; 604/280
[58] Field of Search .................... 604/43-45, 604/51-53, 158-170, 272-275, 280-284

[56] References Cited

U.S. PATENT DOCUMENTS

| | | | |
|---|---|---|---|
| 2,922,420 | 1/1960 | Cheng | 604/272 |
| 3,506,007 | 4/1970 | Henkin | 604/51 |
| 3,670,729 | 6/1972 | Bennett et al. | 604/53 |
| 4,014,333 | 3/1977 | McIntyre | 604/43 |
| 4,072,146 | 2/1978 | Howes | 604/158 X |
| 4,149,535 | 4/1979 | Volder | 604/43 |
| 4,299,217 | 11/1981 | Sagae et al. | 604/44 |
| 4,318,402 | 3/1982 | Vaillancourt | 604/275 |

FOREIGN PATENT DOCUMENTS 960932 1/1975 Canada.

Primary Examiner—Dalton L. Truluck
Attorney, Agent, or Firm—Sughrue, Mion, Zinn, Macpeak and Seas

[57] ABSTRACT

A multi-lumen epidural catheter includes a flexible inner tube 10 having a tip opening 12 and a surrounding flexible outer tube 11 having a pair of side openings 13 spaced upstream from the tip. An anesthetic solution may be injected through the separate flow and discharge paths defined by this structure to deaden a more elongate zone of a patient in a precisely controlled manner.

1 Claim, 3 Drawing Sheets

FIG. 2
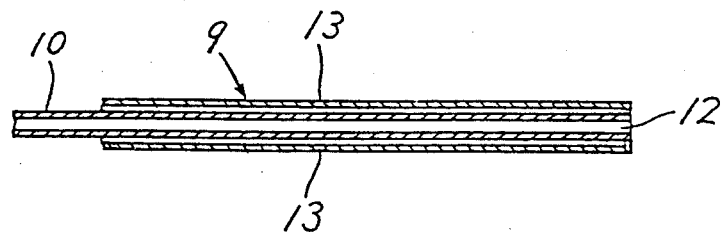
FIG. 3
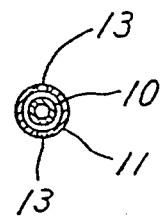
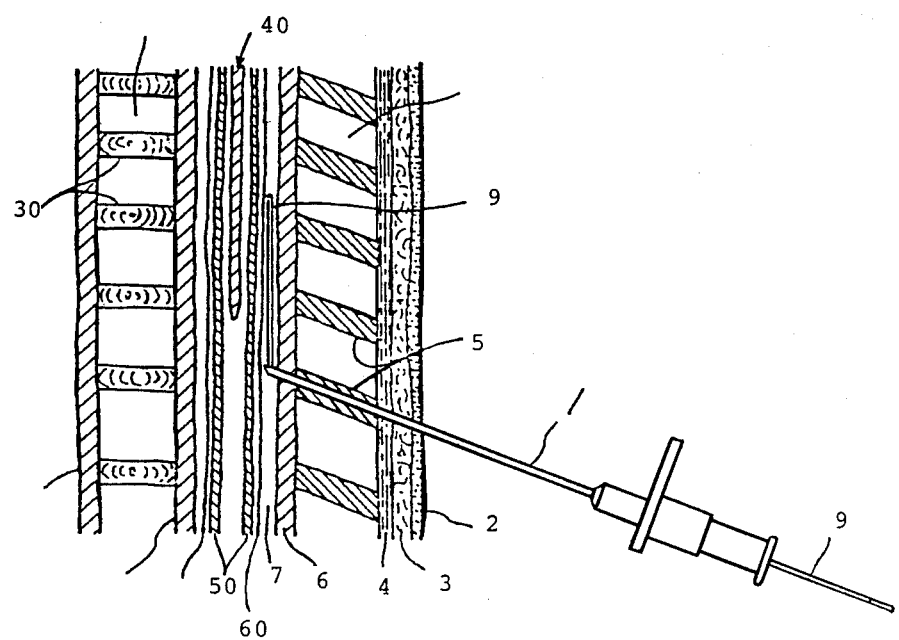
FIG. 4

MULTI-LUMEN EPIDURAL CATHETER

This is a division of application Ser. No. 445,616, filed Nov. 30, 1982, which is a continuation of application Ser. No. 218,987, filed Dec. 22, 1980, both now abandoned.

BACKGROUND OF THE INVENTION

1. Field of the Invention

The present invention relates to a multi-lumen epidural catheter suitable for use in continuous epidural anesthesia, more particularly to a double-lumen epidural catheter capable of controlling anesthesia.

2. Brief Description of the Prior Art

When the spinal nerve of the human is to be anesthesized, an epidural catheter having an injection opening for the inflow of an anesthetic drug or solution only at the tip thereof has been heretofore employed. However, such an epidural catheter necessarily involves a disadvantage in that the anesthetic drug accumulates as an undesirably large droplet around the opening of the catheter, whereas the peripheral portion of a region to be anesthesized receives relatively little anesthetic drug as it is seen in FIG. 5(b), and as a result, anesthesia is non-uniformly achieved. This disadvantage becomes more serious particularly when regional anesthesia is desired to be effected over a wide region, it is then necessary that the droplet size of the anesthetic drug be made large, and a large amount of the anesthetic drug is thus required.

SUMMARY OF THE INVENTION

An object of this invention is to provide a multi-lumen epidural catheter which eliminates the above-described disadvantage. the degree of anesthesia, if desired, with change of time.

Another object of this invention is to provide a multi-lumen epidural catheter capable of controlling an anesthetic region and the degree of anesthesia, if desired, with change of time.

In accordance with this invention, it has now been found that these objects can be accomplished by a multi-lumen epidural catheter which comprises at least one inner tube having a tip and a rear portion for forming a first path for an anesthetic solution, and an outer tube having a tip and a rear portion forming a second path for an anesthetic solution between the inner and outer tubes, wherein the inner tube has an opening at the tip thereof, the outer tube has at least one pair of side openings at portions appropriately spaced from the tip of the outer tube, and the inner tube is separated from the outer tube at the rear portions thereof so that openings for inflow of anesthetic solution into each of the tubes are provided at the rear portions of the inner and outer tubes, respectively.

BRIEF DESCRIPTION OF THE DRAWING

FIG. 2 is an enlarged axially sectional view of the tip of the catheter shown in FIG. 1.

FIG. 3 is an enlarged radially sectional view of the catheter with side openings.

FIG. 4 is an explanatory view showing the catheter in accordance with this invention shown in FIG. 1 in use.

DETAILED DESCRIPTION OF PREFERRED EMBODIMENT

Figure 1:
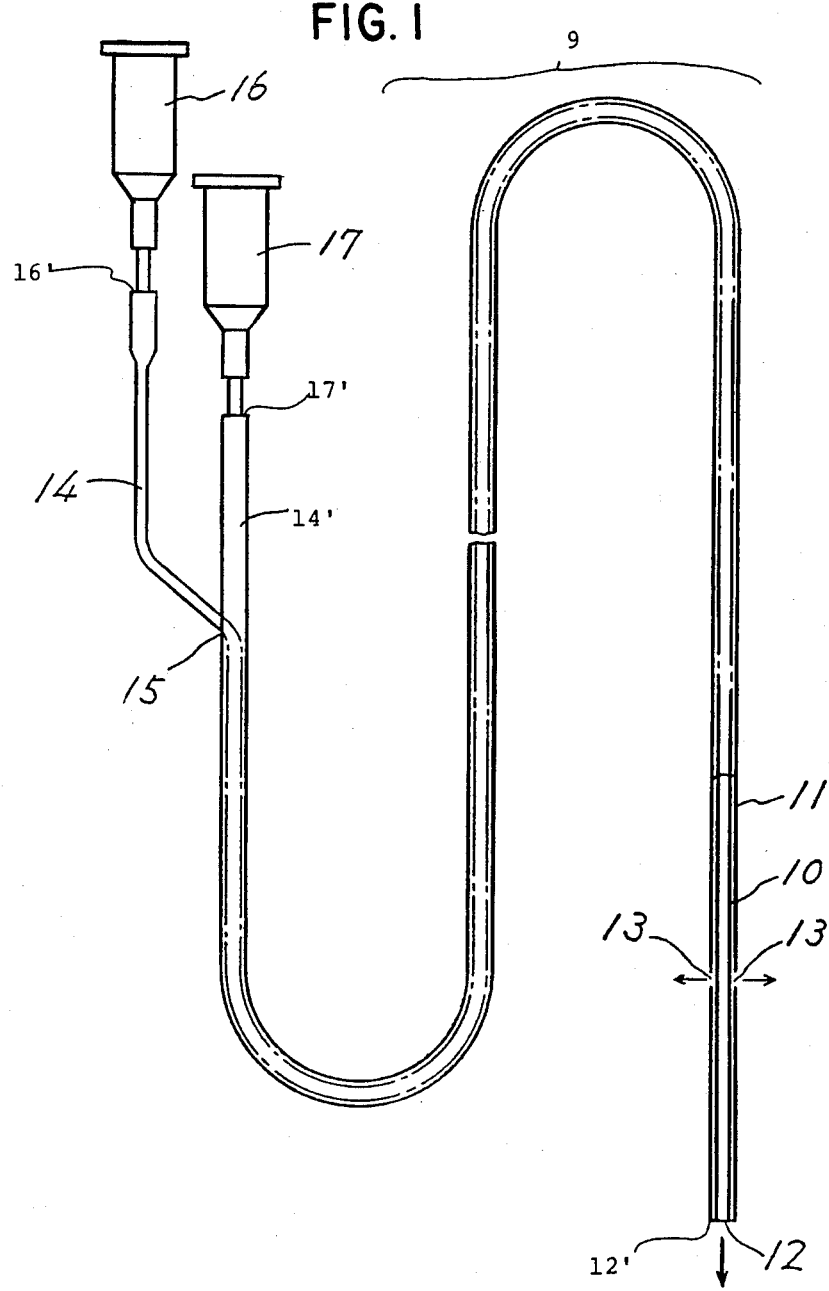
FIG. 1 is a side view of a double-lumen epidural catheter in accordance with this invention, which is partially cut off.

Only for purposes of simplicity, a description is made with reference to a double-lumen epidural catheter.

Referring to the figures, reference numeral 9 denotes an epidural catheter which comprises an inner tube 10 having a tip 12 and a rear portion (14) which is molded using flexible plastics and which forms a first path for an anesthetic solution, and an outer tube (11) having a tip 12' and a rear portion 14' which is made of flexible plastics and which forms a second path for an anesthetic solution between the inner tube 10 and the outer tube 11. The outer tube 11 possesses a diameter determined such that it can smoothly go through an epidural needle 1 to thereby make it easy to locate the catheter 9 in the epidural space 7, as shown in FIG. 4.

As is seen from the above description, the size of the inner tube 10 primarily depends upon the volume of an anesthetic solution required and the rate of injecting the anesthetic solution, and this in turn determines the size of the outer tube 11, and the size of the epidural needle 1. However, from a practical standpoint, there is a certain limit for the size of the epidural needle 1 since the pain caused by inserting the epidural needle 1 into the patient should preferably be minimized. Thus, the size of the epidural needle 1 is automatically fixed in a certain range, and generally between 15 and 18 gauge, preferably 17 gauge. This size range of an epidural needle conversely determines successively the size of the outer tube and then the inner tube. A 17 gauge needle has an outer diameter of about 1.47 mm and an inner diameter of about 1.17 mm. Considering that an anesthetic solution is generally injected at a rate of about 10 ml/min. (though the injection rate slightly varies depending upon personnel, condition of the patient, degree of anesthesia required, etc., the variation in the injection rate can easily be appreciated by one skilled in the art.), it is desired that the inner and outer tubes be of a size sufficient to provide an anesthetic solution at a rate of about 10 ml/min. For example, it is desired that the size of the inner tube 10 be in a range of about 0.2 to about 0.6 mm, preferably 0.4 mm as an inner diameter, and in a range of about 0.4 to 0.8 mm, preferably 0.6 mm as an outer diameter; and the size of the outer tube 11 be in a range of about 0.6 to about 1.0 mm, preferably 0.8 mm as an inner diameter thereof and in a range of about 0.8 to about 1.2 mm, preferably 1.0 mm as an outer diameter. The size relation among the inner tube, outer tube and epidural needle can afford an effective regional anesthesia contemplated in this invention.

Reference numeral 12 denotes an opening at the tip 12 of the inner tube 10 and reference numeral 13 denotes a pair of side openings having an appropriate spacing from the tip 12, e.g., approximately 5 cm distance. While the distance is somewhat varied, one can easily determines the distance from the tip 12 from which an anesthetic solution is spread, because the epidural catheter in accordance with this invention is applied to the human body and the organs are located in a limited area with a relatively fixed positional relation.

Reference numeral 14 is the rear portion of the inner tube 10 separated from the outer tube 11 at the rear portion 14' of the outer tube 11 so that an opening 16' for the inflow of an anesthetic solution is connected to a device 16 at the rear portion 14 thereof. Reference numeral 17 is a device for providing an anesthetic solution therefrom which is connected to the opening 17' at the rear portion 14' of the outer tube 11.

The inner and outer tubes are generally molded using flexible plastics such as polymers of tetrafluoroethylene (generic name: teflon). It is preferred that the flexible plastics be transparent since undesirable back current of blood which might occur during anesthesia using epidural catheters can easily be detected with the naked eye.

While the structure of the epidural catheter of this invention is described with reference to a double-lumen type, it is not limited thereto but also includes a triple lumen epidural catheter. In this case, three different regions can be anesthesized simultaneously or separately. In a similar manner, a multi-lumen epidural catheter can also be employed for achieving anesthesia at controlled regions, simultaneously or separately, depending upon the number of lumens used. In determining the structure of the multi-lumen type, the same principle, considering a volume of an anesthetic solution required and an injection rate of the anesthetic solution, as used in the double-lumen type, also applies to the multi-lumen type. However, from a practical standpoint and demand for type of anesthesia, a double-lumen type is most preferred.

Figure 5A:
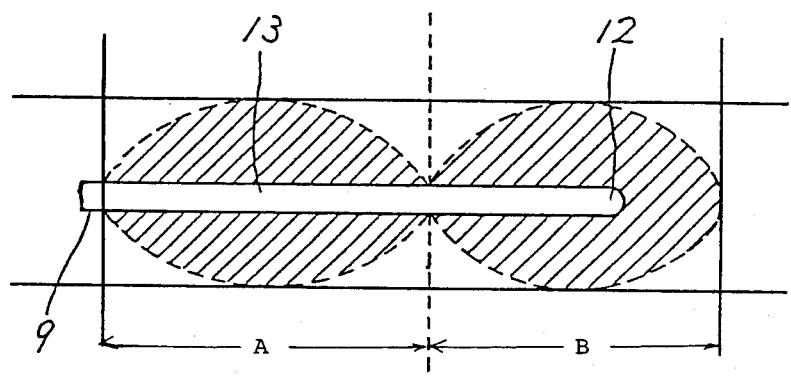
FIG. 5 (a) is an explanatory view showing the state at the time when a drug is being injected using the catheter in accordance with this invention shown in FIG. 1.
FIG. 5(b) is an explanatory view of the state at the time when a drug is injected using a conventional epidural catheter having only one opening at the tip thereof.

The side openings 13 provided on the outer tube 11 form a droplet as shown in FIG. 5(a) which can afford severely controlled anesthesia at required regions and at the same time minimize the volume of the anesthetic solution required. It is preferred that each of the side openings possesses a diameter of about 0.4 to about 0.8 mm, preferably 0.6 mm which can ensure the required injection rate (about 10 ml/min) for an anesthetic solution.

The double-lumen epidural catheter 9 having the structure described hereinabove is employed by injecting an anesthetic solution, simultaneously or separately, using a syringe (not shown) from the respective openings 16' and 17', while detaining the portion including the tip opening 12 and the side openings 13 in the epidural space 7 through the epidural needle 1.

In more detail, as shown in FIG. 4, the epidural needle 1 is introduced slowly and gradually. The needle 1 which can make it easy to locate the catheter 9 in the epidural space 7 passes successively through the skin 2, subcutaneous tissue 3, interspinous ligament 5 and ligamentum flavum 6 to finally reach the epidural space 7. After epidural placement of the needle 7 has been assured (at this time, a negative pressure is loaded, unlike a positive pressure loading when the needle 1 is being passed through from the skin to the ligamentum flavum, so that the epidural placement can be confirmed), the epidural catheter 9 is then introduced into the epidural space 7 through the needle 1. The epidural catheter is inserted about 5 cm into the epidural space. Thereafter, the needle 1 is withdrawn from the skin. An anesthetic drug or solution is injected from the openings 16' (which forms the first path) and 17' (which forms the second path), respectively. If desired, anesthesia can be achieved simultaneously or independently. When the anesthetic solution is to be filled between segments A and B as shown in FIG. 5(a), the injected anesthetic solution forms two round droplets around the two side openings 13 provided on the outer tube 11. Then, the anesthetic solution spreads more smoothly in the segments A and B. Accordingly, the double-lumen epidural catheter of this invention can greatly decrease the required volume of the anesthetic solution for filling the solution in the segments A and B.

Figure 5B:
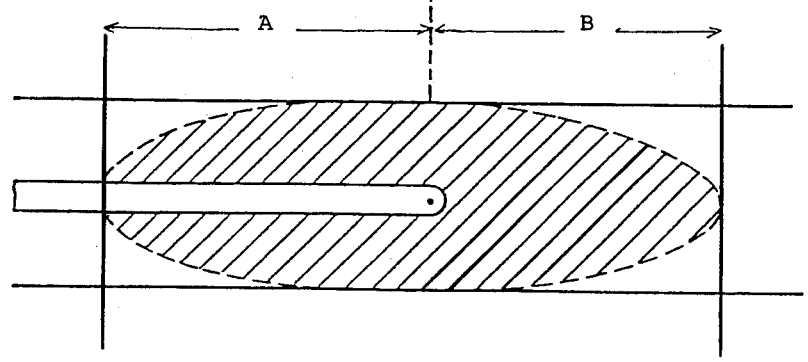

To the contrary, when using the prior art epidural catheter (having only one opening at the tip thereof), it is necessary to inject a large volume of an anesthetic solution since the anesthetic solution is supplied through only one opening at the tip thereof. Thus, the anesthetic solution undesirably accumulates very heavily around the opening at which the anesthetic solution is introduced and the peripheral portion of the anesthetic droplet is very thin, as shown in FIG. 5(b). Therefore, the region for anesthesia cannot be severly controlled with the prior art catheter and of course, there is a danger that the use of an anesthetic solution in a large volume, which is inevitable with the prior art catheter to obtain regional anesthesia, might be accompanied by side effects.

The multi-lumen epidural catheter in accordance with this invention provides the following advantages.

(1) The spread of an anesthetic drug is greater than with the prior art catheter. Thus, the dosage of an anesthetic drug can be decreased so that side effects of the anesthetic drug can be minimized.

(2) During an operation, it is often necessary to expand the anesthetic region because the focus spreads over a wider area than expected prior to the operation. In such a case, it is possible to expand the anesthetic region by injecting an anesthetic drug from the proximal or distal openings of the catheter.

(3) Continuous epidural anesthesia has been used for pain relief in childbirth labor. This is because labor is divided into three stages. A first stage lasts from the onset of the time at which the cervix attains full dilatation. A second stage lasts from the time of the full dilatation to the time at which the baby has been expelled. A third stage lasts from the time of delivery of the baby to the complete expulsion of the placenta. Pain at the first stage is primarily due to dilatation of the cervix. Pain at the second stage is produced by distension of the lower birth canal, vulva and perineum. Pain at the third stage is primarily due to the uterus contraction. During the first stage, block can be limited to the lower thoracic and upper lumbar segments, but during the second stage, the block should be extended to the sacral segments. If a perfect anesthesia is requested in labor, it was necessary to insert two epidural catheters into the epidural space, one catheter serving for the pain relief of the lower thoracic and the upper Clumbar segments and another catheter for the sacral segments. The use of two epidural catheters is very troublesome and the patient suffers a pain stimulus very seriously.

The epidural catheter in accordance with this invention possesses at least two openings for the inflow of an anesthetic solution. When the epidural catheter of this invention is used for the pain relief of labor, it is possible to obtain pain relief using only one opening for the inflow of an anesthetic solution during all the stages of labor. Anesthesia in the lower thoracic and upper lumbar regions is obtained by injecting an anesthetic solution from the proximal opening. At the second and third stages of labor, anesthesia in the vulva and perineum are obtained by injecting an anesthetic solution from the distal opening.

(4) In epidural anesthesia, the insertion of an epidural catheter is performed blindly. Accordingly, the tip of the inner tube sometimes tends to go astray into the intervertebral space (not shown) out of the epidural space 7. In this case, no anesthetic effect is obtained even though an anesthetic solution is injected.

In case of using the epidural catheter of this invention, there is no problem even if the tip opening (12) goes stray in the intervertebral space since the side openings (13) can remain in the epidural space and in this case, an anesthetic solution can be injected through the side openings (13) to effect anesthesia contemplated.

In FIG. 4, reference numerals other than referred to hereinabove are used to mean the following:
- 30: interspinous cartilage
- 40: spinal chord
- 50: arachnoid
- 60: dura While the invention has been described in detail and with reference to specific embodiments thereof, it will be apparent to one skilled in the art that various changes and modifications can be made therein without departing from the spirit and scope thereof.

What is claimed is:

1. A method for continuous epidural anesthesia, comprising the steps of:
   (a) inserting a rigid, hollow epidural needle (1) successively through a patient's skin (2), subcutaneous tissue (3), interspinous ligament (5) and ligamentum flavum (6) until the tip of the needle reaches an epidural space (7),
   (b) introducing a double-lumen epidural catheter (9) through the needle, out through a lateral opening in the tip of the needle, and into the epidural space to a length of about 5 cm,
   (c) said epidural catheter comprising:
      (1) at least one flexible inner tube having a tip and a rear portion forming a first path for an anesthetic solution, and a flexible outer tube having a tip and a rear portion forming a second path for an anesthetic solution between said inner and outer tubes,
      (2) said inner tube having an opening at the tip thereof,
      (3) said outer tube having at least one pair of side openings at portions spaced from the tip of the outer tube a distance not exceeding the length of an epidural space, and
      (4) said inner tube being separated from said outer tube at the rear portions thereof so that openings for the inflow of an anesthetic solution into each of said tubes are provided at the rear portions of said inner and outer tubes, respectively, said inner tube having an inner diameter of about 0.2 to about 0.6 mm and an outer diameter of about 0.4 to about 0.8 mm, and said outer tube having an inner diameter of about 0.6 to about 1.0 mm and an outer diameter of about 0.8 to about 1.2 mm, and
   (d) introducing an anesthetic solution through the rear portions of the inner and outer tubes, through the first and second paths defined thereby, and into the epidural space through the tip opening (12) of the inner tube and the side openings (13) of the outer tube such that contiguous droplets of anesthetic solution form around said tip opening and side openings, the total volume of anesthetic solution necessary to anesthetize a given length of epidural space being less than that required using a catheter having a single fluid outlet.

* * * * *